United States Patent [19]

Appelbaum

[11] Patent Number: 4,803,165
[45] Date of Patent: Feb. 7, 1989

[54] NIF PROMOTER OF FAST-GROWING RHIZOBIUM JAPONICUM

[75] Inventor: Edward R. Appelbaum, Madison, Wis.

[73] Assignee: Lubrizol Genetics, Inc., Wickliffe, Ohio

[21] Appl. No.: 763,800

[22] Filed: Aug. 7, 1985

[51] Int. Cl.⁴ .................. C12N 15/00; C12N 1/20; C12P 21/00; C07H 15/12
[52] U.S. Cl. .................. 435/172.3; 435/68; 435/320; 435/252.2; 435/252.33; 536/27; 935/29; 935/30; 935/41; 935/56; 935/64; 935/67; 935/72
[58] Field of Search .......... 435/172.3, 68, 317; 935/23, 27, 30, 35, 64, 67; 536/27; 439/253, 320

[56] References Cited

U.S. PATENT DOCUMENTS 4,448,885  5/1984  Schuepf et al. .................. 935/29

OTHER PUBLICATIONS

Ruvkun et al (1980), "Cluterspecies Homology of...", PNAS 77:191–95.
Hoennecke, H. (1981), "Recombinant Plasmids Carrying Nitrogen Fixation Genes from R. Japonicum", Nature 291:354–55.
Drummond et al. (1983), "Positive Control... of the nifLA Promoter...", Nature 301: 302–307.
Sundaresan et al (1983), "Activation of... Nitiogenase Promoters...", DNAS 80: 4030–34.
Sinon et al (1983) "Vector Plasmids..." in Molecular Genetics of Bact.–Plant Cluteraction, Puhler A. (ed).
Selvaraj et al. (1983), "Suicide Plasmid Vectors...", J. of Bacteriol, 156: 1292–1300.
Truong et al. (1984), "Isolation... of the Human Prolactin Gene", EMBOJ 3:429–37.
Karin et al. (1982), "Human Metallothionein Genes...", Nature 299:797–802.
Sundaresan et al. (1983), "K. pneumonia nif A product...", Nature 301: 728–731.
Fuhrmann et al. (1982), "Coding Properties of Cloned Nitrogenase...", Melgengenet 187: 419–425.
Better, M. et al. (1983), Cell 35:479–485.
Legocki, R. P. et al. (1984), Proc. Natl. Acad. Sci. USA 81:5806–5810.
Fuhrman, M. et al. (1984), J. Bact. 158:1005–1011.

Primary Examiner—Charles F. Warren
Assistant Examiner—David T. Fox
Attorney, Agent, or Firm—Greenlee and Associates

[57] ABSTRACT

The promoter of the nifH gene of the fast-growing Rhizobium japonicum strain USDA 191, has been cloned. Over 4.2 kilobase pairs (kbp) of DNA were sequences (FIG. 1). Sequences encoding nifH and the 5'-end of nifD were identified, as were sequences involved in promoting operon transcription and a nifH ribosome binding site. Use of the nifH promoter to drive transcription in Rhizobium of heterologous structural genes is taught. Useful sequences and plasmids are also disclosed.

21 Claims, 4 Drawing Sheets

```
   1 ACATGAGAATTCCTTTGGGCAGGGTCGGGGACGCAGAAGAAGTCGCCGAGGCTGCCTACT 60
  61 TTCTGGCCTCGTTTGATGCCTCCTACATCAACGGCTCGATCCTGCACGTGGACGGAGGCT 120
 121 TGATCTCGTCCAGAGAAGCGGGGTGGGGCAGCGAAGTCGATGGAGCAATTTCGACGGAGA 180
 181 TGAGGCCGCAGCGCCGGCCGGCGGCGCGATGGCGGTTGCTCTCTCCCTGAATTGCATTTG 240
 241 CACGCTTTTAGCGCTTGGCGCCTGAATGCGTTAGGGGGCCATGAGCAGGGCCATAGGGAA 300
 301 ACCTTCTCGTCAATCGAGGCGCGACCCACGACTGCGCGATTCCAGATCCGAAAACAAGGA 360
 361 AACACCATGGAGTTCGCAACGTTCATTCTCGCTGCCCAGCGCGGCTATCATCAGTCTTCC 420
 421 GCTAGCGTCGTCCGCAACTCGATAGAGCAGGCAATTTTTTCGGAGCAGGCTGGCTTCAGC 480
 481 ACAGCCTGGTACGCCGAGCACCACTTCAACAACTACAGTCTCGTCCCGTCGCCATTACTG 540
 541 ATGGTAGCCCACTGTGCCGGATTGGCGAGCACCATTCGGCTCGGAACCGCAGTCTGCGTG 600
 601 CTGCCGCTCTACCAACCACAGCGCCTGCTGGCGGAAATCGGCTTTGTCGACGTCGTTGCC 660
 661 AACGGTCGACTCGAACTCGGCGTTGGCTCGGATACCAGCAGTTCGAGTTCGACCGCTTC 720
 721 GGCGTCAATATAGATGAGGCGCCGGCCATCTTTTCGGAATGCCTGGACATTTTGCTGAAG 780
 781 GGACTAAAGCAAAGAATCTTCACCCACAGCGGTCGCTACATGCAGATACCCCCGACGGCG 840
 841 ATTTCGGTGCGCACCCTCCAAAAGCCGACGCCACCGATCTGGATTGCTAGCGCATCCTCC 900
 901 AAAACTATGGCCCGAGCCTATCGTGAGGGTCACAATCTTTTCGTCACGGCTCTCCATGAC 960
 961 GGCTTGGAAACTCTGGGCTTGCTGCGTGGCATCATTAAGACCGCCGCTGCATCCGAGGGC 1020
1021 AAGGAGGTTCGCGACTCCAAGGTATCGCTACTGCCGGTGCTGCTATGCCAGTGATGATGGA 1080
1081 GCGGAAATCAACAGCTATATCGATAACGCCCGCTTCCAGCGCCGGCTGTCCGAGGCACTG 1140
1141 CGACAGCGTCGGCAACAAAGTAAGGACGGCTATATGTTGGAGGAGATGCCGACGCATCAG 1200
1201 GATCTATCGTTCGACACTATGCGCAAGAACCTGCCCATTGGCAGTATCAATCGCGTGATT 1260
1261 GATCGCCTTCTGGAGGAGATCGATGTCTTGAAGCCGGACCAGATTGCAATTCAGACCCAG 1320
1321 CTGGAGAGATTTTGACCAAAACACGATGTTGCGCCAGATCGAGCTTTGGGGAGACAAGATA 1380
1381 ATCCCGGCAGTCCAGAAATCTCTCGGGCAGTCGCAGGCTTGAGTTTATACCGTCCTGACC 1440
1441 TTCGGGTCAGCTCACTTCCTCAGGCGCCGTCAGAATGCCCGGCAAGTTTCAAAAGCCATC 1500
1501 GTAAATGTCGGCACACAGATTACAGCTGAACTCCTCGTGAAAGTGGCTCATGGGCGTCATGG 1560
```

FIG. 1-1

```
   1 ACATGAGAATTCCTTTGGGCAGGGTCGGGGACGCAGAAGAAGTCGCCGAGGCTGCCTACT 60
  61 TTCTGGCCTCGTTTGATGCCTCCTACATCAACGGCTCGATCCTGCACGTGGACGGAGGCT 120
 121 TGATCTCGTCCAGAGAAGCGGGGTGGGGCAGCGAAGTCGATGGAGCAATTTCGACGGAGA 180
 181 TGAGGCCGCAGCGCCGGCCGGCGGCGCGATGGCGGTTGCTCTCTCCCTGAATTGCATTTG 240
 241 CACGCTTTTAGCGCTTGGCGCCTGAATGCGTTAGGGGGCCATGAGCAGGGCCATAGGGAA 300
 301 ACCTTCTCGTCAATCGAGGCGCGACCCACGACTGCGCGATTCCAGATCCGAAAACAAGGA 360
 361 AACACCATGGAGTTCGCAACGTTCATTCTCGCTGCCCAGCGCGGCTATCATCAGTCTTCC 420
 421 GCTAGCGTCGTCCGCAACTCGATAGAGCAGGCAATTTTTTCGGAGCAGGCTGGCTTCAGC 480
 481 ACAGCCTGGTACGCCGAGCACCACTTCAACAACTACAGTCTCGTCCCGTCGCCATTACTG 540
 541 ATGGTAGCCACTGTGCCGGATTGGCGAGCACCATTCGGCTCGGAACCGCAGTCTGCGTG 600
 601 CTGCCGCTCTACCAACCACAGCGCCTGCTGGCGGAAATCGGCTTTGTCGACGTCGTTGCC 660
 661 AACGGTCGACTCGAACTCGGCGTTGGCTCGGGATACCAGCAGTTCGAGTTCGACCGCTTC 720
 721 GGCGTCAATATAGATGAGGCGCCGGCCATCTTTTCGGAATGCCTGGACATTTTGCTGAAG 780
 781 GGACTAAAGCAAAGAATCTTCACCCACAGCGGTCGCTACATGCAGATACCCCCGACGGCG 840
 841 ATTTCGGTGCGCACCCTCCAAAAGCCGACGCCACCGATCTGGATTGCTAGCGCATCCTCC 900
 901 AAAACTATGGCCCGAGCCTATCGTGAGGGTCACAATCTTTTCGTCACGGCTCTCCATGAC 960
 961 GGCTTGGAAACTCTGGGCTTGCTGCGTGGCATCATTAAGACCGCCGCTGCATCCGAGGGC 1020
1021 AAGGAGGTTCGCGACTCCAAGGTATCGCTACTGCGGTGCTGCTATGCCAGTGATGATGGA 1080
1081 GCGGAAATCAACAGCTATATCGATAACGCCCGCTTCCAGCGCCGGCTGTCCGAGGCACTG 1140
1141 CGACAGCGTCGGCAACAAAGTAAGGACGGCTATATGTTGGAGGAGATGCCGACGCATCAG 1200
1201 GATCTATCGTTCGACACTATGCGCAAGAACCTGCCCATTGGCAGTATCAATCGCGTGATT 1260
1261 GATCGCCTTCTGGAGGAGATCGATGTCTTGAAGCCGGACCAGATTGCAATTCAGACCCAG 1320
1321 CTGGGAGATTTTGACCAAAACACGATGTTGCGCCAGATCGAGCTTTGGGGAGACAAGATA 1380
1381 ATCCCGGCAGTCCAGAAATCTCTCGGGCAGTCGCAGGCTTGAGTTTATACCGTCCTGACC 1440
1441 TTCGGGTCAGCTCACTTCCTCAGGCGCCGTCAGAATGCCCGGCAAGTTTCAAAAGCCATC 1500
1501 GTAAATGTCGGCACAGATTACAGCTGAACTCCTCGTGAAAGTGGCTCATGGGCGTCATGG 1560
```

FIG. 1-2

```
1561 GTCGCATACCATTCGCACGACAGACAAGCAGGCTACCGGCGGCAGTACGCATTTGAGCTC 1620
1621 CGATAGTTCAGTCCGCGATTTTAATCGGACGAGGGCCGGAAATAGCCATCTTAAGCAAAC 1680
1681 TTGATCGGACGGCGGACACTTAGGGCTGGCAAAGCCTCCGAGAAGATGCTCCCCAAACCC 1740
1741 GCGGCTTGTACCTGATCAGCGGCAGTGGGCTCCGAGCGCCTGATAGGCAACGCTTTCGAC 1800
1801 AATTGTTTGTGAAATTGTCGGCTCCGCGACACAGGCTTGCGTCTGGGTCGGCTACTTCTC 1860
1861 CTAATCTAAGTAGCTGTAAAAGAAAGTAAACCAGCTTCTGCTGGGCTCACCCTCCTCGAC 1920
1921 TTGGCACGGGTCTTGTAGCCACTCTTGTGCAGGCGGCTTGAGCTGTCCGCTGTATTCGTG 1980
1981 TTGCGGGCAACCGCGATGGTTTCGAACAACGAAGGAAAGCAACATGGCAGGTCTGCGTCA 2040
2041 AATCGCGTTTTACGGCAAGGGCGGTATCGGCAAGTCCACCACCTCGCAGAACACGCTCGC 2100
2101 CGCCCTTGTCGACCTCGGGCAGAAGATCCTCATCGTCGGCTGCGATCCCAAGGCCGACTC 2160
2161 CACCCGGCTCATCCTCAACGCGAAGGCGCAGGACACGGTCCTGCATCTGGCGGCCAAGGA 2220
2221 GGGATCGGTGGAAGATCTCGAGGTCGAGGACGTGCTCAAGGTCGGCTACAAGGGCATCAA 2280
2281 ATGCGTCGAGTCCGGCGGCCCCGAACCGGGCGTCGGCTGCGCCGGCCGCGGCGTCATCAC 2340
2341 CTCGATCAACTTCCTGGAGGAAAATGGCGCCTATGACGATGTCGACTACGTCTCCTACGA 2400
2401 CGTGCTGGGCGACGTGGTGTGCGGCGGCTTCGCGATGCCGATCCGCGAGAACAAGGCGCA 2460
2461 GGAAATCTACATCGTCATGTCCGGCGAGATGATGGCGCTCTATGCCGCCAACAACATCGC 2520
2521 CAAGGGGATCCTCAAATACGCCCATTCGGGCGGCGTGCGGCTCGGCGGGCTGATTTGCAA 2580
2581 CGAGCGCCAGACGGACCGCGAGCTCGATCTCGCCGAGGCGCTGGCGGCCAAGCTCAATTC 2640
2641 CAGGCTCATCCACTTCGTGCCGCGCGACAACATCGTCCAGCACGCCGAGCTCAGGAAGAT 2700
2701 GACGGTGATCCAGTATGCCCCGGAGTCGCAACAGGCTGCGGAGTATCGCGCGCTGGCCGA 2760
2761 CAAGATCCATGCCAATTCCGGCCAGGGCACCGTCCCGACCCCGATCACCATGGAGGAGCT 2820
2821 GGAGGACATGCTGCTCGATTTCGGCGTCATGAAGCCAGCGAGCAAGTGCTTGCCAGAACT 2880
2881 TCAGGCCAAGGAAGCGGCGGCAGCGGCCCAGTGACCGCCGCCGCAGACGCTGCCCGGGAC 2940
2941 GGTGATCCGGTGCGACATTCCACCGAATGGTGCCTCTTCTTGGAGGACACGCAAAAAAGG 3000
3001 GGGCAGGCCAATGAGCCTCGATTACGAGAATGACAGTGCGCTCCATCAGGAGCTGATCAC 3060
3061 GCAAGTGCTGTCGCAGTACCCACACAAGGCGGCCAAGCGTCGCCAAAAGCACCTCAGTGT 3120
3121 CGCATCAGGCCGCGAGGCGGTCGGGGAGGAGGGCGACTGACTCTTATACACAAGXXXXXX 3180
```

FIG. 1-3

```
3181 XXXXXXGTGTATAAGAGTCAGGGAGGGCGAGACCCTCTCCGAATGCGACGTGAAGTCGAA 3240
3241 CATCAAGTCGATCCCCGGGGTGATGACGATCCGCGGCTGCGCCTATGCGGGCTCGAAGGG 3300
3301 CGTGGTCTGGGGCCCGGTCAAGGATATGGTCCACATCTCGCACGGCCCGGTTGGCTGCGG 3360
3361 TCAGTATTCCTGGTCGCAGCGCCGCAACTATTATGTCGGCACCACCGGCGTCGACACCTT 3420
3421 CGTGACGATGCAGTTCACCTCCGACTTTCAGGAGAAGGACATCGTCTTTGGTGGCGACAA 3480
3481 GAAGCTGGAACAGGTCATCGACGAGATCGAGGAGCTGTTTTCCCTCAACAACGGCATCAC 3540
3541 CATCCAGTCCGAATGTCCGATCGGCCTGATTGGCGACGACATCGAAGCGGTGTCGCGCAA 3600
3601 GAAGGCCGTCGAACACGAAACGACGATCGTGCCGGTGCGCTGCGAAGGCTTCCGCGGCGT 3660
3661 CTCGCAGTCGCTCGGCCATCACATCGCCAACGACGCCATCCGCGACTGGGTGTTCGACAA 3720
3721 GGCGGACGACAAGACGGACGTCGAGTTCGAAACCGGTTCCTACGATGTCAACGTCATCGG 3780
3781 CGATTACAACATCGGCGGCGCCTGGGCGTCGCGCATCCTGCTCGAGGAGATCGAGCTGCG 3840
3841 CGTCGTCGGCAACTGGTCGGGCGACGCCACGCTCGCGGAAGTGGAGCGAGCCCCCAGGGC 3900
3901 CAAGCTCAACCTCATCCACTGCTACCGGTCGATGAACTACATCTGCCGGCACATGGAGGA 3960
3961 AAGATACGCCATCCCCTGGATGGAATACAACTTCTTCGGCCCCTCCCAGATCGAAGCCTC 4020
4021 TCTGCGCAAGATAGCCAGGCATTTCGGCCCGACGATCGAAGAACGGGCCGAGAGGTCAT 4080
4081 CGCCAAGTACCGGCCGCTGGTCGACGCCGTGATCGACAAGTACTGGCCGCGCCTCCAGGG 4140
4141 CAAGCGAGTGATGCTCTATGTCGGTGGTTTGCGCCCCCGCCACGTCATCACCGCCTATGA 4200
4201 GGACCTCGGCATGCAGA 4217
```

FIG. 2

RHIZOBIUM NIF PROMOTER REGIONS

| | | | |
|---|---|---|---|
| 191 nifH | CCTCGACT<u>TGGCACG</u>GGTC<u>TTG</u>TAGCCACTCTTGTG | 74bp ------ | ATG |
| Rt nifH | AGCTCAAT<u>TGGCACG</u>ACGC<u>TTG</u>AAAATTGTTCTCGG | 71bp ------ | ATG |
| Rm nifH | CAGACGGC<u>TGGCACG</u>ACT<u>TTTG</u>CACGATCAGCCCTG | 67bp ------ | ATG |
| 110 nifD | TGAGACCC<u>TGGCATG</u>CCGG<u>TTG</u>CAAAGTCTTGGATC | 44bp ------ | ATG |
| 110 nifH | TTAGACC<u>TTGGCACG</u>GCTG<u>TTG</u>CTGATAAGCGGCAG | 149bp ------ | ATG |
| RP nifH | GACAGTG<u>TTGGCATG</u>GCGA<u>TTG</u>CTGTTGAGTTGCAG | 148bp ------ | ATG |

NIF PROMOTER OF FAST-GROWING RHIZOBIUM JAPONICUM

FIELD OF THE INVENTION

Biological nitrogen fixation in the root nodules of leguminous plants is a major component of world food production and therefore practical applications of this field are of major interest.

Prokaryotes can use a wide variety of nitrogen compounds as sole sources of cellular nitrogen. This variety includes ammonia, dinitrogen and nitrate among the inorganic compounds, and proline, arginine and glutamine among complex organic compounds. Each species can utilize a different array of nitrogen compounds. Glutamine, glutamate and aspartate are the key nitrogen compounds in intermediary metabolism. The latter two are the starting compounds of many pathways of amino acid biosynthesis and serve as amino group donors in many reactions. In all other cases the amino group is donated by glutamine. The major enzyme required for the assimilation of ammonia produced by $N_2$ fixation is glutamine synthetase, which catalyses the reaction:

$$\text{Glutamate} + NH_3 + ATP \rightarrow \text{glutamine} + ADP + Pi.$$

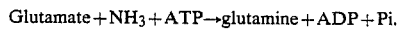

At high $NH_4^+$ concentrations ($>1$ mM) glutamate dehydrogenase is also found. Utilization of the assimilated ammonia depends on the activity of glutamate synthase catalyzing:

$$\text{Glutamine} + \text{2-ketoglutarate} + NADPH \rightarrow 2 \text{ glutamate} + NADP^+$$

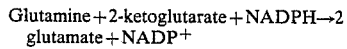

Since ATP is hydrolysed, these reactions have a favorable equilibrium and allow the use of ammonia in the medium or ammonia derived enzymatically from other nitrogen sources (Meers, J. et al. (1970) *J. Gen. Microbiol.* 64:187–194). The formation of ammonia is thus a key step in the biological nitrogen cycle.

Biological nitrogen fixation can be achieved by a variety of microorganisms and occurs through the induction of an enzyme complex, nitrogenase, which converts atmospheric nitrogen to ammonia. This conversion occurs in a group of physiologically diverse prokaryotes, including facultative anaerobes (e.g., *Klebsiella pneumoniae* and *Rhodospirillum rubrum*), obligate anaerobes (e.g., *Clostridium pasteruianum*), obligate aerobes (e.g., *Azotobacter vinelandii*) and some strains of blue-green algae (e.g., *Anabaena cylindrica*) (Sprent, J. I. (1979) *The Biology of Nitrogen Fixing Organisms*, London, McGraw-Hill, pp. 8–11). While this enzyme complex is common to all characterized nitrogen fixing organisms, the conditions under which it is expressed vary considerably between species (Burns, R. C., Hardy, R. W. F. (1975) Nitrogen fixation in bacteria and higher plants, Springer-Verlag, Berlin). The first stages of nitrogen fixation, conversion of nitrogen into ammonia, are achieved symbiotically in the root nodules of leguminous plants which contain the nitrogen-fixing bacteria of the genus Rhizobium. Some non-leguminous plants, e.g., alder, also have interactions with symbiotic bacteria which are nitrogen fixers. In addition, free-living bacteria, e.g., *Klebsiella pneumoniae* and the photosynthetic blue-green bacteria, also fix nitrogen. Biological nitrogen fixation in the root nodules of leguminous plants is a major component of world food production (Burris, R. H. (1980) In *Free Living Systems and Chemical Models; Nitrogen fixation*, Newton, W. E., Orme-Johnson, W. H., eds., Baltimore, University Park Press, pp. 7–16).

The symbiotic association between plants and bacteria of the genus Rhizobium is the result of a complex interaction between the bacterium and its host, requiring the expression of both bacterial and plant genes in a tightly coordinated manner (Vincent, J. M. (1980) In *Symbiotic Associations and Cyanobacteria, Nitrogen Fixation* Vol. 2, W. E. Newton and W. H. Orme-Johnson, eds., Baltimore, University Park Press, pp. 103–129; and Verma, D. P. S., et al. (1981) In *Current Perspectives in Nitrogen Fixation* A. H. Gibson, W. E. Newton, eds., Canberra, Australian Academy of Science, pp. 205–208). In free-living Rhizobia, nitrogenase synthesis is repressed and is only induced after the symbiotic relationship has been established. Furthermore, some Rhizobium species only interact with a narrow range of plant species, whereas other species interact with a wide range.

Bacteria bind to the emerging plant root hairs and invade the root tissue through the formation of an infection thread. The plant responds to this infection by the development of a highly differentiated root module. These nodules are the site of synthesis of the nitrogenase complex. Following nitrogen fixation, the fixed nitrogen is exported into the plant tissue and assimilated by the plant derived enzymes (Scott, D. B., et al. (1976) *Nature* 263:703–705).

Most Rhizobium symbioses are confined to leguminous plants. Furthermore, Rhizobium strains which fix nitrogen in association with the agriculturally-important temperate legumes are usually restricted in their host range to a single legume genus. However, some strains of Rhizobium have been isolated which can fix nitrogen in a diverse group of legume species but can also form an effective symbiosis with non-legumes.

Despite the ability of certain plants to induce nitrogenase activity in a symbiotic relationship with some species of Rhizobium, the genetic analysis of biological nitrogen fixation has previously been confined to free living nitrogen fixing organisms, in particular *Klebsiella pneumoniae*. There are 17 linked nitrogen fixation (nif) genes arranged in at least 7 transcriptional units in the nif cluster of Klebsiella (Kennedy, C., et al. (1981) In *Current Perspectives in Nitrogen Fixation*, A. H. Gibson and W. E. Newton, eds., Canberra, Australian Academy of Science, pp. 146–156; and Reidel, G. E., et al. (1979) *Proc. Natl. Acad. Sci. USA* 76:2866–2870). Three of these genes, nifH, nifD and nifK, encode the structural proteins of the nitrogenase enzyme complex (viz. the Fe-protein subunit (dinitrogenase reductase) and the α- and β-subunits of the Mo-Fe protein (dinitrogenase) respectively. Dinitrogenase is an $\alpha_2\beta_2$ tetramer in which the two non-identical α and β subunits have similar molecular weights of 55,000 to 60,000. Dinitrogenase reductase is a dimer of two identical subunits each having a molecular weight around 35,000. These genes are linked on the same operon in *K. pneumoniae* and are transcribed from a promoter adjacent to the nifH gene. A similar situation (nifHDK) was found in two fast-growing Rhizobia, *R. meliloti* (Ruvkun, G. B., et al. (1982) *Cell* 29:551–559) and *R. leguminosarum* (Schetgens, T. M. P. et al. (1984) *Advances in Nitrogen Fixation Research*, Veeger, C. and Newton W. E., eds., Martinus Nijhoff/Dr. W. Junk Publishers, The Hague, p. 699). In the slow-growing *R. japonicum*, it has been found that nifDK forms one operon and that nifH is located elsewhere on the genome (Fuhrmann, M. and H. Hennecke (1982) Mol. Gen. Genet. 187:419-425). A similar observation was made with another member of the slow-growing rhizobia, Rhizobium sp. Parasponia: a nifH region was found not be linked to nifD (Scott, K. F., et al. (1983) DNA 2:141-148). Yet a different arrangement was detected in the cyanobacterium *Anabaena* sp. 7120, in which nifHD is separated from nifK (Rice, D., et al. (1982) J. Biol. Chem. 257:13157-13163). The remainder of symbiotic genes contain information required for bacterial attachment, root hair curling, initiation and development of nodules and establishment of symbiotic relationships. In addition, regulatory sequences such as promoters, operators, attenuators, and ribosome binding sites are found adjacent to the coding regions. These regulatory sequences control the expression of the structural genes, i.e., the coding sequences downstream in the 3'-direction of the DNA reading strand.

Soybean-nodulating Rhizobium species are classified as *R. japonicum*. Older literature references to *R. japonicum* refer to strains characterized as "slow-growing" Rhizobia. More recent studies of biochemical and genetic characteristics have led to reclassification of "slow-growing" Rhizobia in the genus Bradyrhizobium (Jordan, D. C. (1982) Int. J. Syst. Bacteriol. 32:136). Furthermore, certain "fast-growing" strains have been found which are classified as *R. japonicum* on the basis of their ability to nodulate *Glycine Max cv. Peking*, an undeveloped Asian cultivar of soybeans. One such "fast-growing" strain, USDA 191, has been found able to form fix+ (nitrogen fixing) nodules on commercial soybean cultivars, e.g., Williams (Yelton et al. (1983) J. Gen. Microbiol. 129:1537-1547). Since the literature sometimes refers to slow-growing (Bradyrhizobium) strains simply as *R. japonicum*, confusion may occur. For clarity herein, "slow-growing" commercial soybean nodulating strains, such as USDA 110 or USDA 123, are termed *Bradyrhizobium japonicum* strains, while USDA 191, a "fast-growing" strain, is termed a *Rhizobium japonicum* strain. *R. japonicum* USDA 191 is much more amenable to genetic manipulation than B. japonicum strains because it grows faster, many of the primary genes for symbiosis are located on a plasmid (Appelbaum et al. (1985) J. Bact. 163:385) and transposon mutagenesis occurs at higher frequencies in *R. japonicum* than in *B. japonicum*.

The discovery and study of plasmids, restriction enzymes, ligases and other enzymes involved in DNA synthesis has led to the rapidly developing field of genetic engineering. Use of these techniques has made it possible to transfer DNA across species boundaries, either from eukaryotic to prokaryotic organisms or vice versa. Alternatively, it has been possible to synthesize nucleotide sequences and to incorporate these synthetic sequences into living organisms where they have been expressed. For example, expression in *E. coli* has been obtained with DNA sequences coding for mouse dihydrofolate reductase (Chang, A. C. Y., et al. (1978) Nature 275:617-624) and for hepatitis B virus antigen (Burrell, C. J., et al. (1979) Nature 279:43-47). Two mammal hormones have also been produced in bacteria by use of synthetic DNA (Itakura, K., et al. (1977) Science 198:1056; and Goeddel, D. B., et al. (1970) Proc. Natl. Acad. Sci. USA 76:106).

The practical application of DNA recombination requires the success of a number of different features. First, it must be possible to recognize the DNA fragment coding for the compound of interest and it must be possible to isolate the DNA fragment. Second, it is necessary to understand the mechanisms which control the expression of the information on that DNA fragment and to be able to transfer that information to the control of regulatory sequences which will maximize the productive capabilities of that information. This increased productive capacity could be by rearrangement of coding information and regulatory information within the same organism or between different organisms. The organisms involved may be prokaryotic or eukaryotic. Third, the conversion of coding information into useful products, such as storage proteins and hormones, must occur in an environment where they are not subsequently degraded.

BACKGROUND OF THE INVENTION

In bacteria of the genus Rhizobium, nitrogenase synthesis is normally repressed under free-living conditions and is induced only within a complex symbiosis formed mostly with leguminous plants. *R. trifolii* is an example of a fast-growing Rhizobium with a narrow host range (i.e., clover plants) and cannot normally be induced to fix nitrogen in culture. In contrast, a *Parasponia Rhizobium* species has been isolated and this species is a slow-growing organism with a very broad host range capable of an effective symbiotic relationship with a broad variety of tropical legumes as well as the non-legume Parasponia (Ulmaceae) (Trinick, M. J. (1980) J. Appl. Bacteriol. 49:39-53). *Parasponia Rhizobium* can be induced to fix nitrogen in culture although the level of this fixation is about 100-fold less than can be obtained from the free-living bacterium *Klebsiella pneumoniae*. Other slow-growing Rhizobia include the commercially significant *R. japonicum*, which nodulates soybeans.

The genetics of biological nitrogen fixation have been well characterized in the free-living organism *Klebsiella pneumoniae*. The structural genes for nitrogenase (nifH, nifD and nifK encoding the Fe-protein subunit and the α- and β-subunits of the Mo-Fe protein, respectively) have been mapped both genetically and physically (Kennedy, C. et al. (1981) In *Current Perspectives in Nitrogen Fixation*, Gibson, A. H. and W. E. Newton, eds., Canberra, Australian Academy of Science, pp. 146-156; and Reidel, G. E., et al. (1979) Proc. Natl. Acad. Sci. USA 76:2866-2870). Cloned DNA fragments carrying these sequences have been shown, by Southern blot analysis, to hybridize the homologous sequences in a wide range of nitrogen fixing organisms, including *Rhizobium* (Ruvkun, G. B. and F. M. Ausubel (1980) Proc. Natl. Acad. Sci. USA 77:191-195).

In spite of the ecological diversity of nitrogen fixing organisms, the physiological structure of the nitrogenase enzyme complex appears to be very conserved. In all cases where the enzyme complex has been purified, two proteins are present. The larger protein (dinitrogenase) contains molybdenum, iron and acid-labile sulfur, and carries the binding site for nitrogen and contains two subunit proteins α- and β-coded by the nifD and nifK genes respectively. The smaller protein (dinitrogenase reductase) contains iron and acid-labile sulfur, and is required for the reduction of the dinitrogenase and for the binding of MgATP used in this reduction. The dinitrogenase reductase is coded by the nifH gene. Chemical and spectral analyses of the purified protein components support a conservation of protein structure between organisms (Scott, K. F., et al. (1981) J. Mol. Appl. Genet. 1:71-81). In some cases the structures are sufficiently similar to allow formation of active hybrid enzymes between purified components, e.g., *Azotobacter vinelandii* and *Klebsiella pneumoniae* (Eady, R. R. and B. E. Smith (1979) in A treatise on *dinitrogen fixation* I, II, Hardy, R. W. et al., eds., New York, Wiley Press pp. 399–490). Not surprisingly, therefore, the region of the nif operon coding for dinitrogenase reductase and dinitrogenase α-subunit (nifH and nifD) shows homology at the nucleic acid sequence level with the corresponding sequences in at least 19 other bacterial strains (Ruvkun, G. B. and F. M Ausubel (1980) Proc. Natl. Acad. Sci. USA 77:191–195). Although this conservation of structure is generally true, significant differences between nitrogenases from different organisms also exist as can be shown by variable stability following purification and by the fact that active hybrid complexes do not form in all cases (Eady, R. R. and B. E. Smith (1979) supra).

A DNA fragment carrying the *Klebsiella pneumoniae* nifK, nifD and nifH genes has been isolated from the nif⁻ strain UNF841(Tn5::nifK) (Cannon, F.C. et al. (1979) Mol. Gen. Genet. 174:59–66) and cloned into the *Escherichia coli* plasmid pBR325. The nucleotide sequences of the nifH gene and of 622 nucleotides of the nifD gene were determined (Sundaresan, V. and F. M. Ausubel (1981) J. Biol. Chem. 256:2808–2812; Scott, K. F. et al. (1981) supra). In addition, the DNA sequence of the nifH gene from Anabaena 7120 has been determined (Mevarech, M. et al. (1980) Proc. Natl. Acad. Sci. USA 77:6476–6480). A comparison of the two sequences demonstrates two interesting features: (1) There is very little homology between the two sequences at the nucleotide sequence level although a few stretches (up to 25bp) are conserved, accounting for the observed interspecies homology of the nif genes (Ruvkun, G. B. and F. M. Ausubel (1980) supra); (2) In general, the promoter regions show very little sequence homology with the exception of a short region likely to be involved in common functions, e.g., RNA polymerase recognition.

In contrast, a comparison of the amino acid sequences of the dinitrogenase reductase and of the first 207 amino acids of the α-subunit of dinitrogenase of the two species and of another species show a much greater conservatism. The three species used in this comparison are *Klebsiella pneumoniae* (Kp); Anabaena 7120 (Ab); and *Clostridium pasteurianum* (Cp) (Tanaka, M. et al. (1977) J. Biol. Chem. 252:7093–7100). The Kp and Cp proteins share 67% amino acid sequence homology, Kp and Ab proteins share 71% homology, and the Cp and Ab proteins share 63%. This amino acid sequence homology is not spread evenly throughout the protein. Some regions are virtually identical (90% to 95% homology), while other regions are only weakly conserved (30–35% homology). The structural conservation appears to be centered around the five cysteine residues common to all three Fe proteins. These cysteine residues are believed to be ligands to the active center.

Comparison of the N-terminal amino acid sequence of the α-subunit of dinitrogenase from Cp and Kp shows very little sequence homology in this region. This is in contrast to the very high conservation of amino acid sequence seen in the amino terminal region of the Fe protein. What little homology exists between Cp and Kp α-subunits is confined to regions around cysteine residues, as in the Fe proteins. These homologous regions are thought to be involved in the catalytic functions of the nitrogenase enzyme complex. Therefore, this structural conservatism is thought not to be the result of recent evolution and dispersal of the nif genes (Postgate, J. R. (1974) Sym. Soc. Gen. Microbiol. 24:263–292) but, rather, is postulated to be related to a conservation of function.

A review of comparisons between the known structural gene and promoter sequences in Rhizobia has been published by Schofield, P. and Watson, J. (1985) Nucleic Acids Research 13:3407–3418. Structural studies of cloned Rhizobium nif genes have been reported by Fuhrmann and Hennecke (1984) J. Bacteriol. 158:1005–1011; Kaluza and Hennecke (1984) Mol. Gen. Genet. 196:35–42; Scott, K. et al. (1983) DNA 2:149–155; Scott, K. et al. (1983) DNA 2:141–148; Torok and Kondorosi (1981) Nucl. Acids. Res. 9:5711–5723; Adams and Chelm (1984) J. Molec. and Appl. Genet. 2:392–405; and Quinto et al. (1985) Proc. Natl. Acad. Sci USA 82:1170–1174.

SUMMARY OF THE INVENTION

A recombinant plasmid is disclosed, wherein there is a wide host range vector containing an inserted fragment of DNA including a promoter of a nitrogenase complex gene of *Rhizobium japonicum* USDA 191 and a foreign structural gene under the control of the regulatory region. Since the regulatory region and the foreign genes are carried on plasmids which can be lost from *Rhizobium japonicum* USDA 191, a method for tranferring these genes from a vector to the bacterial chromosome is also described. Novel *Rhizobium japonicum* USDA 191-derived strains are thereby generated, having a chromosomally integrated composite gene including a nitrogenase gene regulatory region and a foreign gene.

BRIEF DESCRIPTION OF THE FIGURES

FIGS. 1-1, 1-2, and 1-3 disclose R. japonicum USDA 191 sequences, including nifH, the promoter and coding region, at least part of nifD, the nifH-nifD intergenic region, the nifD start codon, and $HN_2$-terminal coding region and 5′-flanking sequences. The start of nifH translation is shown by a box around the ATG at positions 2024–2046; the direction of translation is shown by an arrow; the ribosome binding site AAGGA is shown by a line above the sequence; the consensus regions of the nifH promoter are shown by inverted brackets; the stop codon (TGA at 2912–2914) is underlined; the nifD start codon and direction of translation are shown by the box and arrow at 3011–3013.

FIG. 2 compares various nif promoters. Underlining denotes regions of homology; the ATGs at the right are translational start codons. Organisms are indicated as follows: 191, *R. japonicum* USDA 191, a fast-growing strain; Rt, *R. trifolii*; Rm, *R. meliloti*; 110, *R. japonicum* USDA 110, a slow-growing strain; and Rp, Parasponia Rhizobium ANU 289.

DETAILED DESCRIPTION OF THE INVENTION

The taxon *Rhizobium japonicum* can be split into two groups, fast-growing rhizobia and slow-growing rhizobia or "bradyrhizobia" (Jordan, D. C. (1982) Int. J. Syst. Bateriol. 32:136–139). The structural organization of the nif genes in fast-growing strains differs from that of slow-growing rhizobia in that the nifH and nifDK genes which code for the polypeptides of the nitrogenase complex have been shown to be linked in the fast-growers. The fix complex is here defined to include all genes involved in the fixation of nitrogen in a *Rhizo-* bium japonicum/host plant symbiosis. The 5'-end of the nifH operon and 5'flanking sequences, including the operon's promoter of the fast-growing *Rhizobium japonicum* strain USDA191 has been cloned. Over 4.2 kilobase pairs (kbp) of DNA were sequenced (FIG. 1). Sequences encoding nifH and the 5'-end of nifD were identified, as were sequences involved in promoting operon transcription (FIG. 2) and a nifH ribosome binding site. Seven base pairs (bp) upstream from the ATG translation start site of the *R. japonicum* nifH gene (FIG. 1) there is a 5'-AAGGA-3' sequence marking a ribosome binding site (Shine, J. and Dalgarno, L. (1974) Proc. Natl. Acad. Sci. USA71:1342–1346; Stormo, G. D. et al. (1982) Nucl. Acids Res. 10:2871–2996). The nifH open reading frame is terminated by a TGA stop codon and encodes a protein having 299 amino acids homologous to the previously dislosed nifH genes.

The area in front of the transcriptional start does not contain any sequences which are reminiscent of typical *E. coli* RNA polymerase binding sites (Rosenberg, M. and D. Court (1979) Ann. Rev. Genet. 13:319–353). However, the nifHK promoter (a promoter is here defined as the nucleotide sequence upstream from the transcriptional start site containing all the regulatory regions required for transcription) has a sequence 5'-TTGGCACG-4bpTTG-3' 89 nucleotides before the translational start site. (A translational start site is here defined as the ATG-codon translated into a methionine residue at the amino terminus of an open-reading frame and a transcription start site is the first deoxynucleotide to be transcribed into a mRNA sequence.) This promoter sequence unexpectedly showed similarities to a promoter sequence of *Klebsiella pneumoniae* nif genes (Beynon, J. et al. (1983) Cell 34:665–671). Since *K. pneumonia* is a species which does not participate in the bacterial-plant symbiotic relationships for nitrogen reduction, the factors which regulate the activities of the nif genes are likely to be quite different. Beynon et al. proposed that the TTGCA sequence was equivalent to a "Pribnow box" of genes regulated by nitrogen control (Drummond, M. et al. (1983) Nature 301:302–307; Beynon, J. et al. (1983) Cell 34:665–671; Ow, D.W. et al. (1983) Proc. Natl. Acad. Sci. USA 80:2524–2528) and the CTGG sequence may be the recognition target for nif-activating proteins (Beynon, J. et al. (1983) supra). However, the operation of the present invention is not dependent upon the correctness of these proposals. The 191 nifH promoter shares some points of sequence similarity with other Rhizobium nif promoter sequences (FIG. 2). Although there is homology in the short consensus regions, there is little or no homology in other portions of the promoter region and less than 90% homology overall. Recognizing that some base substitutions can occur without substantially affecting function, and that such substitutions or variations from the cloned sequence disclosed herein can occur, a USDA 191 nifH promoter is herein considered to include alternative sequences having nifH promoter function that are at least 90% homologous with the disclosed sequence.

Since the promoter region of the nifH operon has been isolated, characterized and cloned, it is possible to delete the nifH and nifD nitrogenase genes, i.e., the DNA sequences normally transcribed into mRNA or RNA, and replace them with (a) structural gene(s) isolated from an extraneous source, either another structural gene of USDA 191 not under nif promoter control or a structural gene from a source organism other than USDA 191. The extraneous gene(s) thus placed under the control of the nifH promoter can then be inserted into a plasmid vector followed by conjugation into a fast-growing *Rhizobium japonicum* strain. A vector is defined here as a plasmid with a replication origin which carries and replicates one or more fragments of foreign DNA. The extraneous gene is then expressed in this novel *R. japonicum* under conditions where the nif gene promoters are activated. Alternatively, the novel composite gene which includes the foreign structural gene and the nif gene promoter can be integrated with the chromosome of a host *R. japonicum* in order to maximize the stability of the trait conferred by the composite gene.

The novel plasmids disclosed herein are useful for amplifying the quantities of composite genes, for transferring such genes to selected *R. japonicum* or *B. japonicum* host strains, for generating new *R. japonicum* or *B. japonicum* host strains and as intermediates for the construction of plasmids having one or more of the foregoing uses. The *R. japonicum* or *B. japonicum* strains of the present invention are useful for expressing the composite gene, under certain conditions, to provide a useful product, to confer an advantageous property to a plant or to improve the rate, quality or efficiency of the extraneous gene product. In particular, the properties of the novel strains are manifested within root nodules formed by novel *R. japonicum* strains of the invention in symbiotic combination with a host plant. Depending upon the extraneous gene chosen for expression in the nodule, the nodule then serves as a production source for a protein coded by the extraneous gene. Examples of proteins which can be expressed in root nodules include the insect-toxic protein of *Bacillus thuringiensis* (Wong, H. C. et al. (1983) J. Biol. Chem. 258:1960), the hydrogenase found in some but not all Rhizobium strains (Cantrell, M. et al. (1983) Proc. Natl. Acad. Sci. USA 80:181), metallothionein (Karin, M. and R. I. Richards (1982) Nature 299:797–892) and prolactin (Cooke, N. et al. (1981) J. Biol. Chem. 256:4007–4016). The foregoing list is not intended as limiting, but merely as an exemplary of the broad range of possibilities for synthesis of proteins in root and stem nodules of plants. In general, the invention makes it possible to produce any protein that may be of use, either as a product extracted from the nodule, as an excretion product of the nodule, conferring an advantage for the host plant, or as a functional protein within the nodule itself, improving the effectiveness of the symbiotic interaction. In addition to the proteins disclosed herein, others will be apparent to those of ordinary skill in the art, taking advantage of the known or subsequently discovered properties of root nodules and of specific proteins. A major advantage conferred by gene expression under control of a nif regulatory region in root nodules is derived from the inventor's recognition that such expression is regulated in a similar manner as the expression of the nif genes themselves. The foreign gene is only minimally expressed, if at all, in the free living bacteria but is maximally expressed within the root nodule. Furthermore, because of the specific nature of the host-bacterium symbiosis, gene expression occurs only in the selected plant species recognized by the modified bacterial strain. These properties consequently insure, first, that the foreign gene expression provides maximum local effect of the expression product, and second, that environmental side effects are limited since gene expression can be confined to the nodular tissue of the selected soybean plant strain or variety.

EXPRESSION OF EXTRANEOUS GENES DOWNSTREAM FROM THE NIFH PROMOTER OF RHIZOBIUM JAPONICUM

A principle feature of the present invention is the construction of a plasmid having an inserted foreign gene under control of a nif operon promoter. The structural gene must be inserted in the correct position and orientation with respect to the promoter in order to obtain expression of the structural gene controlled by the promoter. Position has two aspects. The first relates to the side of the promoter on which the structural gene is inserted. It is known that the majority of promoters control initiation of transcription and translation in one direction only along the DNA. The region of DNA lying under promoter control is said to lie "downstream" or alternatively on the 3'-side of the promoter. Therefore, to be controlled by the promoter, the correct position of the foreign gene insertion must be "downstream" from the promoter. The second aspect of position refers to the distance, in base pairs, between functional elements of the promoter, for example, the transcription initiation site and the translational start site of the foreign gene. Substantial variation appears to exist between promoters with respect to this distance. Therefore the structural requirements in this regard are best described in functional terms. Optimum spacing can be achieved by experiments varying the length of this distance. As a first approximation, reasonable operability can be obtained when the distance between the promoter and the inserted foreign gene is similar to the distance between the promoter and the gene it normally controls. Orientation refers to the directionality of the structural gene. By convention, that portion of a structural gene which ultimately codes for the amino terminus of a protein is termed the 5' end of the structural gene, while that end which codes for amino acids near the carboxyl end of a protein is termed the 3'-end of the structural gene. Correct orientation of a structural gene is with the 5'-end thereof proximal to the promoter. An additional requirement in the case of constructions leading to fusion protein expression is that the insertion of the structural gene into an existing nitrogenase complex structural gene sequence must be such that the coding sequences of the two genes are in the same reading frame phase, a structural requirement which is well understood in the art.

In order to express extraneous genes on the 3'-side of the nitrogenase complex regulatory sequences, it is first advantageous to construct a doublestranded DNA sequence corresponding to the nifH regulatory sequences. To achieve this, synthetic DNA primer complementary to the ribosome binding site of the m-RNA and extending a few nucleotides to the side thereof is first constructed. Then the cloned nifH fragment is excised from the vector, purified and the excised nifH fragments are ligated into appropriate single stranded DNA phage (e.g., fd) vectors. The resultant recombinant DNA plasmids are then transformed into E. coli strains, and single colonies are propagated. Those colonies which extrude single stranded templates corresponding to the m-RNA strand are isolated. The synthetic DNA is used as a primer on these single stranded templates to generate double stranded DNA by primer extension with DNA polymerase I (Klenow fragment). This double stranded DNA will extend from the ribosome binding site to an indeterminate soint within the single stranded DNA vector. Any single stranded regions are removed by S1 nuclease treatment. Alternatively, a double stranded vector, e.g., pBR322, may be denatured and replicated using the same synthetic DNA primer. If a double stranded vector is used, then suitable precautions well known to those skilled in the art should be used to avoid the presence of background unlabelled fragments, e.g., it is possible to demonstrate the presence of contaminating fragments by use of restriction maps.

Then synthetic EcoRI linkers are ligated to the DNA fragments followed by digestion with EcoRi and that restriction endonuclease (termed endonuclease A for generality) which recognizes the restriction site at the 5'-end of the nifH promoter region. The resultant DNA fragments are then cloned into an EcoRI-endonuclease A cleaved plasmid, transformed into a suitable E. coli host and amplified. The choice of plasmid is based on principles of operating convenience and location of the appropriate restriction sites, as will be understood by those of ordinary skill in the art.

The plasmid is now cleaved with EcoRI and the fragment is cloned into the wide host range plasmid pRK290 to produce a pRK290-nif regulatory fragment construct. Alternatively, another wide host range plasmic, pSUP204, can be used to construct the recombinant nif regulatory plasmid.

Alternatively, the DNA fragments provided with EcoRI restriction endonuclease-specific ends are initially cloned into a mobilizable broad host range vector capable of replication in either E. coli or most other gramnegative bacteria, such as pSUP104 or pSUP204 (Simon, R. et al. (19083) in Molecular Genetics of the Bacteria-Plant Interaction, Puhler, A. ed., pp. 98106). After amplification, the recombinant plasmid is transferred directly to the desired recipient strain.

In order to clone and express extraneous genes, appropriate DNA fragments carrying these extraneous genes are isolated and synthetic EcoRI linkers are ligated to the fragments (EcoRI-foreign gene-EcoRI). These EcoRI-foreign gene-EcoRI DNA fragments are then litigated into EcoRI-cleaved vector DNA, for example, pSUP104 or pSUP204 containing the nif regulatory fragment, resulting in a nif-regulated expression plasmid, pSS104 or pSS204, respectively, and transformed into Escherichia coli. After selection and amplification, the nif-regulated expression plasmid is then transferred with the aid of helper plasmids to the appropriate Rhizobium or Agrobacterium strain by mating.

The exconjugant Rhizobim strains are then used to infect soybean plants or other appropriate legumes which are subsequently assayed for the production of foreign mRNA and/or protein.

Introduction of DNA Sequences Into the Chromosome/Genome of Gram-Negative

Organisms Other Than E. coli

Some plasmids can be lost rather easily from some bacterial strains, thus leading to the loss of expression of those genes carried on the plasmids. One method of stabilizing the expression of certain genes carried on plasmids, or, for that matter, any foreign DNA segment, would be the introduction of such genes or extraneous DNA segments, hereinafter termed "introduced DNA", into the chromosome of the host bacteria. Such a system employs a "suicide vector" and, preferably, a transposon.

Suicide vectors are plasmid molecules which replicate stably in one bacterial host (in this case, Escherichia coli) but fail to replicate in a different bacterial species (e.g., Rhizobium trifolii).

Transposons are genetic elements which are able to move (translocate) from one location to another in DNA. The translocation process is mediated by gene products encoded on the transposon and is dependent upon the intregrity of repeated sequences (directly or indirectly repeated) located at each end of the transposon. Transposons generally carry a gene (or genes) encoding resistance to one (or more) antibiotics. The transposon and the suicide vector are linearized and religated into a single recombinant DNA molecule.

The general method of transferring introduced DNA segments to the chromosome of a gram-negative bacterial strain other than E. coli is outlined here. The DNA fragments to be introduced can be generated in a number of ways: (a) by restriction with site-specific restriction endonucleases; (b) by partial or complete digestion with restriction endonucleases which generate DNA fragments having blunt ends; (c) by digestion of DNA with the enzyme DNAase I in the presence of $Mn^{2+}$ ions thus generating random fragments which are generally blunt-ended; or (d) by shearing the DNA into large fragments.

In the preferred method, the suicide vector carrying a transposon with an antibiotic resistance gene is linearized and the appropriate fragment of introduced DNA is litigated into a "co-integrated recombinant molecule". The fragment of DNA is inserted into a restriction endonuclease site within the transposon in such a manner that the insertion does not disrupt normal transposition nor expression of the drug resistance marker. This ligated DNA is then transformed into an E. coli strain in which it can be amplified and mobilized for transfer into other gram-negative bacteria.

The cloned, introduced DNA fragment from this E. coli strain can then be moved into the chromosome of any gram-negative bacterium, e.g., Rhizobium japonicum. This is most conveniently achieved by the process of bacterial conjugation. The E. coli strain carrying the suicide vector which contains an antibiotic resistance gene is mixed with cells of the antibiotic sensitive gram-negative strain on the surface of a nutrient agar plate. The plate is incubated for a period (4-16 hours) at the optimum temperature of the gramnegative strain and, during this time, cells of each bacterial species come into physical contact (conjugation) and the suicide vector is transferred from the donor E. coli to the recipient gram-negative strain. The cell mixture is washed off the plate and spread on an agar plate which is selective for the antibiotic resistance. It is preferred to include selection means that select against growth of the E. coli parent strain once the conjugation and transfer is completed.

Since the suicide vector containing the introduced fragment of DNA cannot be amplified autonomously in the recipient gram-negative strain, a transfer of genetic material to the bacterial chromosome can occur in one of three ways: (a) If a fragment of the recipient gram-negative bacterial chromosome (BC) has been previously inserted into the suicide vector (SV) thus creating a region of homology between the suicide vector and the recipient gram-negative bacterial chromosome, then a single reciprocal recombination will result in the incorporation or cointegration of the entire recombinant molecule into the chromosome of the recipient gram-negative bacterial chromosome; (b) If a fragment of the recipient gram-negative bacterial chromosome has been previously inserted into the suicide vector thus creating a region of homology between the suicide vector and the recipient gram-negative bacterial chromosome and then an introduced DNA fragment and a drug resistance gene are inserted into this region of homology, a double reciprocal recombination event will incorporate only the introduced DNA fragment and the drug resistance gene into the chromosome of the recipient gram-negative bacterial strain. Such recombination is site-specific, the chromosomal location being determined by the fragment of chromosomal DNA carried on the suicide vector. (c) In the preferred method, the transposon containing an introduced DNA fragment and an antibiotic resistance gene may be transposed into the bacterial chromosome of the recipient gram-negative bacterial strain. In addition, Tn refers to a transposon used to transpose the inserted DNA into the bacterial chromosome. Selection for the antibiotic resistance ensures maintenance of the inserted DNA.

For the sake of convenience and clarity, definitions used are gathered together and presented below:

(a) Nitrogenase complex: all genes involved in the fixation of nitrogen in a Rhizobium japonicum host plant symbiosis.

(b) Promoter: the nucleotide sequence upstream from the transcriptional start site containing all the regulatory regions required for transcription. The promoter region may be partly defined by the technique of S1 nuclease mapping, which identifies the transcription start site. Further definition of the promoter is based on function. Parts of the sequence proximal to the transcription start site are often essential for promoter function while more distal upstream segments may function to provide "fine tuning" response to controlling substances. Certain consensus sequences have been shown to be characteristic of procaryotic promoters (Resenberg and Court (1979) Supra. Other consensus sequences have been found for nif genes by comparison of the nifH promoters of other Rhizobium species. At least 200bp upstream of a consensus region whose sequence is TGGCACGNNNNTTG is needed for full activity (Hennecke, H., personal communication). The foregoing criteria can be used to identify the NifH promoter of R. japonicum USDA 191 with reasonable certainty within the 5' untranslated region upstream from the start of the nifH coding region. S1 nuclease mapping data, obtainable by application of ordinary skill in the art using known techniques, will provide data showing the location of the transcription start site, and deletions farther upstream are used to identify the limits of promoter function at the 5' end distal from the start of the coding region. The USDA 191 nifH promoter is located in the sequence extending from about position 1770 (FIG. 1) to the transcription start site.

(c) Translational start site: the ATG codon translated into a methionine residue at the amino terminus of an open reading frame.

(d) Transcription start site: the first deoxynucleotide to be transcribed into an RNA sequence of an mRNA sequence.

(e) Extraneous gene(s): (a) structural gene(s) isolated either from another gene of USDA 191 not under nif promoter control or from a source organism other than USDA 191.

(f) Vector: a plasmid with a single replication origin which carries and replicates one or more fragments of foreign DNA.

(g) Composite gene: a gene whose structural or regulatory components are derived from different sources.

EXAMPLE 1

Sequence of USDA 191 nifH pEA105 (Appelbaum, E. et al. (1984) in *Advances in Nitrogen Fixation Research,* Veeger, C. and Newton, W. E., eds., p. 670) carries a *Klebsiella pneumoniae* DNA segment carrying nifMVSUXNEYKDHJ. Hybridization of the *K. pneumoniae* nif probe to an EcoRI digest of USDA 191 revealed two strongly hybridizing fragments (4.2 kbp and 4.7 kbp) and several weakly hybridizing fragments (Appelbaum et al. (1984) supra). The 4.2 kbp and 4.7 kbp fragments were missing in a pSym191-cured strain EA213C3, indicating that both are present in pSym191. Prakash, R. K. and Atherly, A. G. (1984) J. Bacteriol. 160:785-787 showed that cloned nifH and nifD genes of *R. meliloti* each hybridize to both the 4.2 kb and 4.7 kb fragments in several fast-growing *R. japonicum* strains and suggested that the nifH and nifD genes are repeated in these strains. A fast-growing *R. japonicum* strain, USDA 191 (Keyser, H. H. et al. (1982) Science 215:1631-1632) was mutagenized by insertion of the transposon Tn5 by mating USDA 191 with *E. coli* strain SM10 (pSUP1011) and transfer of the suicide vector pSUP1011, which carries Tn5, as described by Simon et al. (1983) Biotechnology 1:784-791. One of the resulting kanamycin resistant Tn5 derivatives, EA213, was found to have an insertion of Tn5 into the pEA105-hybridizable 4.2 kbp EcoRI fragment and had a Fix⁻ symbiotic phenotype. The Fix⁻ phenotype of strain EA213 (which contains an insertion of Tn5 in the 4.2 kb fragment) shows that the nif gene(s) or the 4.2 kb fragment is functional in USDA 191 and is not complemented by the nif sequences on the 4.7 kb fragment. This contrasts with the situation of *R. phaseoli,* where insertion mutations in individual copies of repeated nif genes do not result in a Fix⁻ phenotype (Quinto et al. (1985) supra).

EA213 DNA digested with EcoRI was mixed with and ligated to EcoRIlinearized pSUP202 (Simon). *E. coli* transformants were selected for kanamycin resistance and a colony harboring a plasmid designated pEA213-12 was identified. pEA213-12 was found to consist of 3 EcoRI fragments: the pSUP202 vector fragment, the fragment containing Tn5, and a third fragment from elsewhere in the USDA 191 genome. To remove the undesired third fragment, pEA213-12 was digested with EcoRI, treated with alkaline phosphatase, and ligated to EcoRI-digested pBR322. *E. coli* transformants were selcted for kanamycin resistance and a colony harboring a plasmid designated pEA5K2 was identified. This plasmid contains only the Tn5-containing nif fragment and the pBR322 vector fragment. This is the plasmid used for DNA sequencing. HB101 containing pEA5K2 is on deposit. About 4.2 kbp of *R. japonicum* DNA of the Tn5-containing fragment was sequenced (Maxam, A. M. and Gilbert, W. (1980) Meth. Enzymol. 65:499-560; Barker, R. R. et al. (1983) Plant Mol. Biol. 2:335-350); the derived sequence is presented in Table 1. Comparison with known sequences of other nif genes revealed a complete nifH gene (positions 2024 to 2911), a 99 bp intergenic region downstream of nifH, and the first part of nifD (starting at position 3011 and after interruption by Tn5, continuing past the end of the disclosed sequences. Tn5 was inserted in nifD; it and its effects on the *R. japonicum* DNA are represented by the "X"s between positions 3174 and 3186 of FIG. 1 and flanking sequences for up to about 30 bp either side of the "X"s. The nifH structural gene is 88.9% homologous to the nifH gene of *R. trifolii,* and 78.6% homologous to the nifH gene of *R. japonicum* strain USDA 110. The USDA 191 nifH promoter extends from about position 1770 in FIG. 1 to the transcription start.

The 200 base pair region preceding nifH was analyzed for consensus sequences previously found in nif promoter regions in other Rhizobium species. The sequences 5' . . . TGGCACGNNNNTTG . . . 3' was found between 102 and 89 base pairs upstream of the initiation codon of nifH, as expected for a functional nif promoter (FIG. 2). These sequences were not found in the intergenic region between nifH and nifD. Thus, nifH and nifD appear to be part of a single operon in USDA 191, just as they are in other fast-growing rhizobia.

Proteins were purified from the bacterial fractions of USDA 191 and EA213-induced nodules, fractionated on acrylamide gels, and analyzed by western blotting using antisera that are specific for nitrogenase component I (which contains the product of the nifK and nifD gene) or component II (the product of the nifH gene) (antisera were a gift from T. Bissiling and were prepared using *R. leguminosarum* nitrogenase). The component II antiserum reacted strongly with a 35 kD polypeptide that was present in equal amounts in USDA 191 and EA213 nodules, and is presumed to be the nifH gene product of USDA 191. The component I antiserum reacted very strongly with two bands of 54 kD and 62 kD that are presumed to be the products of the nifK and nifD genes and less strongly with two bands of 43 kD and 45 kD that may be degradation products. These 4 bands were completely missing from EA213, indicating that the insertion in nifD has a polar effect on nifK, as previously observed in other Rhizobium species in whick nifK is downstream of nifD in the same operon. These results indicate that nifH, nifD, and nifK form a single functional operon in the region mutagenized in EA213.

EXAMPLE 2

Expression of extraneous genes under the control of a nifH promoter DNA region

Synthesize a DNA primer which is complementary to the ribosome binding site of the *Rhizobium japonicum* nifH gene (5'-GTTGCTTTCCTTCGTTGTTCG-3'). The *R. japonicum*::Tn5 DNA fragment cloned and sequenced in Example 1 is then subcloned as an EcoRI fragment into a single stranded DNA phage (e.g., one of the M13mp-series or an fd derivative), transformed into *E. coli* JM103 and propagated therein. The cloned fragment is amplified and single stranded templates (ca. 1 μg) are recovered from the supernatant following centrifugation of the bacterial host. A 10-fold excess of the synthetic DNA primer in the presence of the four deoxynucleotide triphosphates (one of which is radioactive) and DNA polymerase I (Klenow fragment) is now used as a primer on this nifH template to generate double stranded DNA (dsDNA) (FIG. 10). The mixture is incubated for 15-45 minutes at 25° to 3720 C. during which time the complementaty strand is substantially extended. The remaining single stranded DNA is then removed by digestion with S1 nuclease. EcoRI linkers (GGAATTCC) are then ligated to the double stranded DNA fragments followed by digestion with EcoRI (FIG. 11). The fragments are separated by agarose gel electrophoresis and 2.0 kbp fragment containing sequences 5-' to the nifH gene, including its promoter, is eluted and cloned into the wide host range plasmid pSUP204, which has previously been digested by the restriction enzyme EcoRI. The resulting recombinant plasmid is termed pRHnifH-SUP204. Following transformation and amplification in a suitable *E. coli* host strain, e.g., S17-1 (Simon, R. et al. (1983) Biotechnol. 1:784-791) which is restriction negative, i.e., r−, partial cleavage with EcoRI allows the addition of any foreign structural gene or foreign DNA fragment into the linearized plasmid downstream from the nifH promoter fragment. For example, the *B. thuringiensis* crystal protein gene (see Example 4) or the human prolactin gene can be inserted (Cooke, N. et al. (1981) J. Biol. Chem. 256:4007-4016) or the human metallothionein gene can be inserted (Karin, M. and Richards, R. I. (1982) Nature 299:797-802) resulting in a "composite" recombinant. A composite recombinant is herein defined as a recombinant DNA plasmid containing a vector, a promoter sequence and any extraneous DNA whose expression is under the control of said promoter sequence.

EXAMPLE 3

Insertion of the bacterial toxin gene from Bacillus thuringiensis into the recombinant plasmid pRjnifH-SUP204

Recombinant plasmids containing inserts of the gene encoding the toxic crystal protein of *B. thuringiensis* are obtained using the techniques described (Wong, H. C. et al. (1983) J. Biol. Chem. 258:1960-1967; Schnepf, H. E. et al. (1984) J. Biol. Chem. 260:6264-6272). The recombinant plasmid pES1 (ATCC No. 31995) consisting of the plasmid vector pBR322 and DNA homologous to the 30, 32 and 37 megadalton plasmids, as well as DNA homologous to linearized forms of the very large plasmids of *B. thuringiensis* is partially cleaved with EcoRI to give linear molecules. These partial cleavage products are further restricted by the enzyme AvaI. The digestion conditions are as recommended by the manufacturer. A probe for the toxic crystal protein gene is isolated and radioactively labelled as previously described (Wong, H. C. et al. (1983) supra). The restriction fragments are separated by agarose gel electrophoresis and the labelled probe is found to hybridize to one fragment of approximately 15 kilobases (kb). This fragment includes the EcoRi fragments D and F (wong, H. C. et al., supra). The 15 kb fragment is then cloned into M13mp8 or M13mp9 according to standard procedure (Messing, J. and Vieira, J. (1982) Gene 19:269-276) and transformed into *E. coli* JM103. The single stranded DNA from the extruded phage particles is purified and replicated in vitro by use of a synthetic primer (5'-TGTTATCCA-TGGGTTACCTCC3'). (The general method of site specific mutagenesis is described in Zoller, M. J. and Smith, M. (1982) Nucl. Acids Res. 10:6487-6500.) The resulting double stranded recombinant plasmid is then transformed back into *E. coli* JM103 and amplified. The amplified double stranded plasmid DNA is purified from the *E. coli* JM103 cells and cleaved with the restriction endonucleases NcoI and AvaI. NcoI cleaves at the site of the synthetic primer (which is the initiation site of the toxic crystal protein gene) and AvaI cleaves at a site which is downstream from the 3'-end of the toxic crystal protein gene. The overhangs are then filled in to blunt ends (Maniatis, T. et al. (1975) Proc. Natl. Acad. Sci. USA 72:1184-1188).

Finally, the pRJnifH-SUP204 recombinant plasmid which is derived from pSUP204 is partially cleaved with EcoRI and the overhangs filled in to blunt ends. HindIII linkers are then added to both the *B. thuringiensis* toxic crystal protein gene fragment and to the pRjnifH-SUP204 recombinant. Following the HindIII digestion of both components, the toxic crystal protein gene and the pRjnifH-SUP204 recombinant plasmid are ligated together to give a pRjnifH-SUP204—*B. thuringiensis* toxic crytal protein gene composite. The mixture is transformed into a suitable *E. coli* host, e.g., K802, SM10 or RR1. Plasmids are isolated from individual colonies and the orientation and position of the crystal protein gene are determined by restriction mapping. A colony containing a plasmid with the correct position and orientation is then conjugated to *Rhizobium japonicum* and the plasmid is transferred as already described (Example 2). The production of mRNA and/or the toxic crystal protein is monitored as already described (Wong et. al., supra).

Exemplified above is combination of a complete crystal protein structural gene with a nifH promoter. However, in many cases it may be advantageous to substitute a partial protein gene for the complete gene. Such partial genes have been disclosed by Schnepf, H. E. and Whiteley, H. R. (1985) J. Biol. Chem. 260:6273-6280. Construction of similar partial gene and testing for retention of toxicity are well understood in the art.

EXAMPLE 4

Introduction of DNA sequences into the genome of gram-negative organisms other than *E. coli*

This example is based on the following general principles. Two basic components are required. These are: (1) a suicide vector, and (2) a transposon.

Suicide vectors are plasmid molecules which replicate stably in one bacterial host (in this case, *Escherichia coli*) but fail to replicate in a different bacterial species (e.g., *Rhizobium japonicum*).

Transposons are genetic elements which are able to move (translocate) from one location to another in DNA. The translocation process is mediated by gene products encoded on the transposon and is dependent upon the integrity of repeated sequences (directly or indirectly repeated) located at each end of the transposon. Transposons generally carry a gene (or genes) encoding resistance to one (or more) antibiotics.

In the protocol to be outlined below, use is made of the transposon designated Tn5 and the suicide vector pSUP1011 (Simon, R. et al. (1983) in *Molecular Genetics of the Bacteria-Plant Interaction*, Puhler, A. ed., pp. 98-106).

Transposon Tn5 is a DNA element of 5.7 kilobases (kb) in length, consisting of 1.5 kb inverted repeat sequences flanking a 2.7 kb central region. Encoded within one of the inverted repeats are the functions required for transposition. The central region of the transposon carries a gene conferring resistance to the antibiotic kanamycin (Km$^r$). In the middle of the central region is a DNA sequence which is recognized by the restriction endonuclease BamHI. In the suicide vector pSUP1011, the only site recognized and cut by BamHI is that located within the Tn5 element. Experiments (Simon R. et al. (1983) supra) have shown that insertion of DNA fragments into the BamHI site of Tn5 does not disrupt normal transposition nor expression of the kanamycin-resistance gene of the resultant "hybrid" transposon.

The DNA fragment to be introduced can be generated in a number of ways:

(1) Complete or partial restriction with BamHI, Sau3A, MboI, etc, which generate fragment having the same, complementary, single-stranded ends.

(2) Partial or complete digestion with restriction endonucleases which generate DNA fragments having blunt ends.

(3) Digestion of DNA with the enzyme DNAaseI in the presence of $Mn^{++}$ions which generates random fragments which (generally) are blunt ended.

The suicide vector (pSUP1011) DNA is treated as follows depending on the type of fragment to be cloned (above);

(1) Complete restriction with endonuclease BamHI and treatment with the enzyme alkaline phosphatase.

(2) Complete restriction with BamHI followed by either:
  (a) treatment with S1 nuclease to remove the single-stranded ends, or
  (b) "filling-in" of the single-stranded ends by the enzyme reverse transcriptase in the presence of nucleotide triphosphates.

Each of the above treatments is followed by treatment with alkaline phosphatase.

Cloning: Vector and fragment DNA, prepared as above, are mixed and treated with the enzyme T4 DNA ligase. The ligated DNA is then transformed (introduced) into *Escherichia coli* strain SM10. (This strain is capable of mobilizing (Mob+) pSUP1011 derivatives (recombinant plasmids) into other gramnegative bacteria.) (Simon R. et al. (1983) in *Molecular Genetics of the Bacteria-Plant Interaction*, A. Phler ed., pp. 98–106). The resultant transformants are screened by the Grunstein and Hogness colony hybridization procedure (Grunstein, M. and Hogness, D. S. (1975) Proc. Natl. Acad. Sci. USA 72:3961) to detect those containing the desired cloned DNA fragment.

Introduction of the cloned DNA fragment into the genome of any gramnegative bacterium (e.g., *Rhizobium japonicum*) is achieved via a process called bacterial conjugation. The *E. coli* SM10 derivative, carrying the desired pSUP1011 recombinant, is mixed with cells of (kanamycin-sensitive) *R. japonicum* on the surface of a nutrient agar plate. The plate is incubated for a period (4–16 hours) at a 29°–30° C. (optimum temperature for *R. japonicum*) and during this time cells of each type come into physical contact (conjugation) and the pSUP1011 derivative is transferred from *E. coli* to *R. japonicum*. The cell mixture is washed off the plate and spread on an agar plate which is selective for kanamycin-resistant *R. japonicum*. The resultant colonies will be derivatives of *R. japonicum* in which the cloned DNA fragment, within Tn5, will be inserted at some point in the genome. Selection for kanamycin resistance ensures maintenance of the inserted DNA.

At this stage it is unknown whether the DNA fragment, within Tn5, has been transferred to the chromosome of *R. japonicum* or to one of its several plasmids. This uncertainty can be resolved by separation of the plasmids and the bacterial chromosome by horizontal agarose gel electrophoresis (Djordjevic, M. A. et al. (1982) J. Bacteriol. 151:560–568), transfer of the plasmid DNA and chromosomal DNA to nitrocellulose filters, and hybridization of the filters with a 32P-labelled fragment of Tn5 using methods well understood in the art (Maniatis et al., 1982).

The organism *E. coli* HB101 pEA5K2, described in Example 1 was deposited on July 29, 1985, at the Northern Regional Reseach Center, Peoria, Illinois, Accession No. B-15987.

What is claimed is:

1. A bacterial strain containing and replicating therein a recombinant DNA plasmid capable of functioning as a vector comprising
a composite gene comprising a promoter of a nifH gene from a fast-growing *Rhizobium japonicum* bacterium, and an extraneous structural gene under control of said promoter.

2. A bacterial strain as recited in claim 1 wherein said vector is pRK290.

3. A bacterial strain as recited in claim 1 wherein said nifH promoter is a nucleotide sequence selected from the group consisting of the nucleotide sequence of FIG. 1 from positions 1770 to the transcription start site, and functionally equivalent sequences having at least 90% sequence homology with said nucleotide sequence.

4. A bacterial strain as recited in claim 1 wherein said structural gene is a human prolactin gene.

5. A bacterial strain as recited in claim 1 wherein said structural gene is a human metallothionein gene.

6. A recombinant DNA plasmid capable of functioning as a vector comprising
a promoter of a nifH gene from a fast-growing *Rhizobium japonicum* bacterium.

7. A recombinant DNA plasmid as recited in claim 6 wherein said vector functions are provided by a plasmid selected from the group consisting of pRK290 and pSUP204.

8. A recombinant DNA plasmid as recited in claim 6 wherein said nifH promoter comprises a nucleotide sequence selected from the group consisting of the nucleotide sequence of FIG. 1 from position 1770 to the transcription start site, and functionally equivalent sequences having at least 90% sequence homology with said nucleotide sequence.

9. A recombinant DNA plasmid as recited in claim 6 comprising additionally a structural gene inserted in such orientation and location as to be expressible under control of said promoter.

10. A recombinant DNA plasmid as recited in claim 6 wherein said structural gene is obtained from a Rhizobium species.

11. A recombinant DNA plasmid as recited in claim 6 wherein said structural gene is an extraneous gene.

12. A recombinant DNA plasmid as recited in claim 6 wherein said structural gene is a toxin gene.

13. A recombinant DNA plasmid as recited in claim 6 wherein said toxin gene is a bacterial toxin gene of Bacillus thuringiensis.

14. A composite gene comprising a nifH promoter of *Rhizobium japonicum* USDA 191 having a nucleotide sequence selected from the group consisting of the nucleotide sequence of FIG. 1 from position 1770 to the transcription start site, and functionally equivalent sequences having at least 90% homology with said nucleotide sequence; and an extraneous structural gene.

15. The composite gene of claim 14 wherein the extraneous structural gene comprises a nucleotide sequence derived from *Bacillus thuringiensis* and codes for a protein or peptide toxic to insects.

16. A method for expressing a structural gene under control of a promoter of a nifH gene from a fast-growing *Rhizobium japonicum* bacterium comprising the steps
(a) isolating from a fast-growing *Rhizobium japonicum* promoter of a nifH gene, (b) cloning said promoter of a nifH gene into a wide host range plasmid producing a recombinant DNA plasmid,
(c) isolating a DNA fragment carrying an extraneous structural gene and inserting said DNA fragment into said recombinant DNA plasmid at a position on the 3'-side of said promoter of a nifH gene giving a cointegrated recombinant plasmid, wherein said DNA fragment is so oriented with respect to said promoter of a nifH gene as to be expressible under control thereof,
(d) transforming said co-integrated recombinant plasmid into a Rhizobium japonicum strain capable of a symbiotic relationship with plant cells, and
(e) infecting a soybean plant with said Rhizobium japonicum strain wherein expression of mRNA or protein coded by said foreign structural gene occurs.

17. A method as recited in claim 16 wherein said nifH promoter is selected from the group consisting of the nucleotide sequence of FIG. 1 from positions 1770 to the transcription start site, and functionally equivalent sequences having at least 90% sequence homology with said nucleotide sequence.

18. A method as recited in claim 16 wherein said wide host range plasmid is pRK290 or pSUP204.

19. A bacterial strain having the composite gene of claim 13 incorporated into its chromosal DNA.

20. A bacterial strain of claim 19 selected from the group consisting of strains of *Rhizobia*.

21. A bacterial strain of claim 20 selected from the group consisting of strains of fast-growing *R. japonicum*.

* * * * *

UNITED STATES PATENT AND TRADEMARK OFFICE
CERTIFICATE OF CORRECTION

PATENT NO. : 4,803,165

DATED : Feb. 7, 1989

INVENTOR(S) : Edward R. Appelbaum

It is certified that error appears in the above-identified patent and that said Letters Patent is hereby corrected as shown below:

At the first column on the first page of the patent under "OTHER PUBLICATIONS" at line 1, please rewrite " "Cluterspecies " as --"Interspecies--; At the first column on the first page of the patent under "OTHER PUBLICATIONS" at line 3, please rewrite "Hoennecke," as --Hennecke,--; At the first column on the first page of the patent under "OTHER PUBLICATIONS" at the last two lines of the column, please rewrite "Nitiogenase Promoters . . .", DNAS" as --Nitrogenase Promoters . . .", PNAS--. At the 2nd column on the first page of the patent, line 1, please rewrite "Sinon" as --Simon--; At the 2nd column on the first page of the patent, second line, please rewrite "Cluteraction," as --Interaction,"; At the 2nd column on the first page of the patent, line 12, please rewrite "Melgengenet" as --Mol. Gen. Genet.--; At the 2nd column on the first page of the patent, line 16, please rewrite "Fuhrman," as --Fuhrmann,--; At the second column on the first page of the patent, line 4 under "ABSTRACT" please rewrite "sequences" as --sequenced--. At column 1, line 53, please rewrite "organisms,the" as --organisms, the--. At column 10, line 10, please rewrite "EcoRi" as --EcoRI--; At column 10, line 30, please rewrite "gramnegative" as --gram-negative--; At column 10, line 31, please rewrite "(19083)" as --(1983)--; At column 10, line 32, please rewrite "98106" as -- 98-106 --;

At column 11, line 26, please rewrite "litigated" as --ligated--. At column

UNITED STATES PATENT AND TRADEMARK OFFICE
CERTIFICATE OF CORRECTION

PATENT NO. : 4,803,165

DATED : Feb. 7, 1989

INVENTOR(S) : Edward R. Appelbaum

Page 2 of 2

It is certified that error appears in the above-identified patent and that said Letters Patent is hereby corrected as shown below:

12, line 34, please rewrite "(Resen-" as -- (Rosen- --. At column 13, line 39, please rewrite "EcoRIlinearized" as --EcoRI-linearized--. At column 14, line 59, please rewrite "3720" as --37°--; At column 14, line 60, please rewrite "complementaty" as --complementary--. At column 15, line 44, please rewrite "wong" as --Wong--. At column 17, line 2, please rewrite "fragment" as --fragments--; At column 17, line 30, please rewrite "gramnegative" as --gram-negative--; At column 17, line 32, please rewrite "Phler" as --Puhler--; At column 17, line 39, please rewrite "gramnegative" as --gram-negative--. At column 18, line 68, please insert --a-- before "promoter".

Signed and Sealed this

Twenty-eighth Day of November 1989

*Attest:*

JEFFREY M. SAMUELS

*Attesting Officer*     *Acting Commissioner of Patents and Trademarks*